United States Patent [19]
Kushnaryov et al.

[11] Patent Number: 5,466,672
[45] Date of Patent: Nov. 14, 1995

[54] THERAPEUTIC USE OF CLOSTRIDIUM DIFFICILE TOXIN A

[75] Inventors: Vladimir M. Kushnaryov, Milwaukee; Philip N. Redlich, Shorewood; Sidney E. Grossberg, Milwaukee; J. James Sedmak, Brookfield, all of Wis.

[73] Assignee: Ophidian Pharmaceuticals, Inc., Madison, Wis.

[21] Appl. No.: 44,631

[22] Filed: Apr. 8, 1993

Related U.S. Application Data

[63] Continuation-in-part of Ser. No. 985,321, Dec. 4, 1992.

[51] Int. Cl.$^6$ .......................... C07K 7/08; C07K 14/195; A61K 38/10; A61K 39/08
[52] U.S. Cl. ............................. 514/14; 530/327; 530/409; 530/825
[58] Field of Search ............................. 514/14; 530/825, 530/409, 327

[56] References Cited

U.S. PATENT DOCUMENTS

| | | | |
|---|---|---|---|
| 4,650,674 | 3/1987 | Aggarwal et al. | 424/85 |
| 4,894,443 | 1/1990 | Greenfield et al. | 530/388 |
| 4,962,188 | 10/1990 | Frankel | 530/389 |
| 5,087,616 | 2/1992 | Myers et al. | 514/21 |

OTHER PUBLICATIONS

S. Donta et al., "Differential Effects of *Clostridium difficile* Toxins on Tissue–Cultured Cells," J. Clin. Microbiol. 15:1157 (1982).
C. Fiorentini et al., "Effects of *Clostridium Difficile* Toxins A and B on Cytoskeleton Organization in HEp-2 Cells: A Comparative Morphological Study," Toxicon 27:1209 (1991).
H. Krivan and T. Wilkins "Purification of *Clostridium difficile* Toxin A by Affinity Chromatography on Immobilized Thyroglobulin," Infect. Immun. 55:1873 (1987).
V. M. Kushnaryov et al., "Reversibility of Action of *Clostridium Difficile* Toxin A on Cho Cells and Intermediate Filaments in Nuclei," Proc. 46th Ann. Meeting Electron Microscopy Soc. Amer., 1988, p. 134.
A. Lima et al, "*Clostridium Difficile* Toxin A Interactions with Mucus and Early Sequential Histopathologic Effects in Rabbit Small Intestine," Laboratory Investigation 61:419 (1989).
A. Lima et al., "Effects of *Clostridium difficile* Toxins A and B in Rabbit Small and Large Intestine in Vivo and on Cultured Cells in Vitro," Infect. Immun. 56:582 (1988).
S. W. Rothman et al., "Differential Cytotoxic Effects of Toxins A and B Isolated from *Clostridium difficile*", Infect. Immun. 46:324 (1984).
J. Torres et al., "Sensitivity in Culture of Epithelial Cells from Rhesus Monkey Kidney and Human Colon Carcinoma to Toxins A and B from *Clostridium Difficile*," Toxicon 30:419 (1992).
Boring et al., Cancer Statistics, Cancer J. Clin. 42:19 (1992).
Macdonald et al., "5–Fluorouracil, Adriamycin, and Mitomycin–C (FAM) Combination Chemotherapy in the Treatment of Advanced Gastric Cancer," Cancer 44:42 (1979).
Gerlach et al., "Multidrug Resistance," Cancer Surv. 5:25 (1986).
Goldie and Coldman, "The Genetic Origin of Drug Resistance in Neoplasms: Implications for Systemic Therapy," Cancer Res. 44:3643 (1984).
Gottesman and Pastan, "Resistance to Multiple Chemotherapeutic Agents in Human Cancer Cells," Trends Pharm. Sci. 9:54 (1988).
Fischerman et al., "Survival among patients with Liver Mestastases from Cancer of the Colon and Rectum," Scand. J. Gastroent. Suppl. 37:111 (1976).
Anai et al., "Sensitivity Test for 5–Fluorouracil and Its Analogues, 1–(2–Tetrahydrofuryl)–5–Fluorouracil, Uracil/1–(2–Tetrahydrofuryl)–5–Fluorouracil (4:1) and 1–Hexylcarbamoyl–5–Fluoroacil, Using the Subrenal Capsule Assay," Oncology 45:144 (1988).
Lyerly et al., "*Clostridium difficile:* Its Disease and Toxins," Clin. Microbiol. Rev. 1:1 (1988).
Dove et al., "Molecular Characterization of the *Clostridium difficile* Toxin A Gene," Infect. Immun. 58:480 (1990).
Fiorentini and Thelestam, "*Clostridium Difficile* Toxin A and its Effects on Cells," Toxicon 29:543 (1991).
Kushnaryov and Sedmak, "Effect of *Clostridium difficile* Enterotoxin A on Ultrastructure of Chinese Hamster Ovary Cells," Infect. Immun. 57:3914 (1989).
Kushnaryov et al., "Actin and Iamin Comprised Filaments in the Nuclei of Chinese Hamster Ovary Cells Affected with *Clostridium difficile* Enterotoxin A," Cytobios 64:181 (1990).
Fiorentini et al., "Interaction of *Clostridium difficile* Toxin A with Cultured Cells: Cytoskeletal Changes and Nuclear Polarization," Infect. Immun. 58:2329 (1990).
Kushnaryov et al., "Cytotoxicity of *Clostridium difficile* Toxin A for Human Colonic and Pancreatic Carcinoma Cell Lines [1]," Cancer Res. 52:5096 (1992).
Redlich et al., "Selective Cytotoxicity of *Clostridium difficile* Enterotoxin A for Cancer Cell Lines of Gastrointestinal Tract Origin," Proc. Am. Assoc. Cancer Res. (1992).
Wren et al., "Antigenic Cross–Reactivity and Functional Inhibition by Antibodies to *Clostridium difficile* Toxin A, Streptococcus Mutans Glucan–Binding Protein, and a Synthetic Peptide," Infect. Immun. 59:3151 (1991).
V. Kushnaryov et al., "Cytotoxicity of Clostridium Difficile Entertoxin A: Unusual Intranuclear Structures in Cho Cells," Abstracts, P13.3.12, Fourth International Congress of Cell Biology, Montreal, Quebec, Canada, Aug. 14–19, 1988.
V. Ling, "P–Glycoprotein–Mediated Multidrug Resistance to Cancer Chemotherapy," Advances in Oncol. 9:3 (1993).
N. Sullivan et al., "Purification and Characterization of Toxins A and B of *Clostridium difficile*," Infect. Immun. 35:1032 (1982).
S. Donta and S. Shaffer, "Effects of *Clostridium difficile* Toxin on Tissue–Cultured Cells," J. Infect. Diseases 141:218 (1980).

*Primary Examiner*—Jill Warden
*Assistant Examiner*—Carol A. Salata
*Attorney, Agent, or Firm*—Haverstock, Medlen & Carroll

[57] ABSTRACT

Methods for treating cancer are described, including methods for treating colon and pancreatic cancer. Bacterial toxins and portions of bacterial toxins are employed as both diagnostic and therapeutic agents.

7 Claims, 5 Drawing Sheets

THERAPEUTIC USE OF CLOSTRIDIUM DIFFICILE TOXIN A

RELATED APPLICATION DATA

This application is a continuation-in-part application of copending application Ser. No. 07/985,321, filed Dec. 4, 1992, pending.

FIELD OF THE INVENTION

The present invention relates to methods for treating cancer, and particularly colon and pancreatic cancer.

BACKGROUND

Carcinomas of the gastrointestinal tract are a leading cause of cancer deaths in the United States. Colorectal and pancreatic cancer are estimated to constitute over 75% of all gastrointestinal tract cancers diagnosed in 1992. See generally Boring et al., Cancer J. Clin. 42:19 (1992).

As with other types of cancer, attempts have been made to control gastrointestinal cancer with chemotherapeutics. 5-Fluorouracil has been the agent most widely used in the treatment of these types of tumors. See J. S. Macdonald et al., Cancer 144:42 (1979).

Success with chemotherapeutics as anticancer agents generally has been hampered by the phenomenon of multiple drug resistance, resistance to a wide range of structurally unrelated cytotoxic anticancer compounds. J. H. Gerlach et al., Cancer Surveys 5:25 (1986). The underlying cause of progressive drug resistance may be due to a small population of drug-resistant cells within the tumor (e.g., mutant cells) at the time of diagnosis. J. H. Goldie and A. J. Coldman, Cancer Research, 44:3643 (1984). Treating such a tumor with a single drug first may result in a remission, where the tumor shrinks in size as a result of the killing of the predominant drug-sensitive cells. With the drug-sensitive cells gone, the remaining drug-resistant cells continue to multiply and eventually dominate the cell population of the tumor.

It is now known that drug resistance is due to a membrane transport protein, "P-glycoprotein," that can confer general drug resistance. M. M. Gottesman and I. Pastan, Trends in Pharmacological Science, 9:54 (1988). Phenotypically, over time, the tumor cells show a reduced cellular accumulation of all drugs.

The problem of drug resistance is no less significant in attempts to treat colon cancer with 5-fluorouracil. Indeed, metastases from the primary colon/rectal tumor are particularly resistant to this drug, leading many to conclude that secondary colon cancer (e.g., liver metastases) cannot be cured. K. Fischerman et al., Scand. J. Gastroent. Suppl. 37:111 (1976).

Use of 5-fluorouracil derivatives also has complications; in many cases, tumors that are resistant to 5-fluorouracil are also resistant to 5-fluorouracil analogues. H. Anai et al., Oncology 45:144 (1988). Furthermore, 5-fluorouracil and its derivatives have significant inherent toxicity. They do not specifically eliminate cancer cells; rather, they affect all replicating cells of the body.

What is needed is an approach to gastrointestinal cancer that is reliably tumoricidal. Importantly, the treatment must be effective with minimal host toxicity.

SUMMARY OF THE INVENTION

The present invention relates to methods for treating cancer, and particularly colon and pancreatic cancer. In accordance with the present invention, a member from the class of bacterial toxins is selectively employed in soluble form to treat tumor patients in vivo. The proposed treatment is expected to have many of the effects of recognized chemotherapeutic agents—however, with greater specificity and without the associated development of drug resistance.

The present invention contemplates, in a preferred embodiment, using soluble *Clostridium difficile* toxin A to treat gastrointestinal tumors. In this embodiment, the toxin is administered (intravenously, intramuscularly, intrathecally, intraperatoneally, etc.) in a therapeutic preparation.

The present invention also contemplates using soluble *Clostridium difficile* toxin A in combination or sequentially with other pharmaceuticals (e.g., chemotherapeutic agents) to treat cancer. In one embodiment, the method comprises administering a therapeutic preparation comprising a mixture of soluble toxin A and 5-fluorouracil. In another embodiment, the method comprises administering soluble toxin A to patients previously treated with 5-fluorouracil.

The present invention further contemplates using soluble *Clostridium difficile* toxin A before and/or after surgical removal of the primary tumor. In one embodiment, the method comprises administering toxin A after surgery as adjunct therapy.

The present invention also contemplates using an in vitro assay to screen gastrointestinal tumors for sensitivity to toxin A. In one embodiment, this comprises culturing patient tumor cells in the presence of the toxin.

DESCRIPTION OF THE INVENTION

Figure 1:
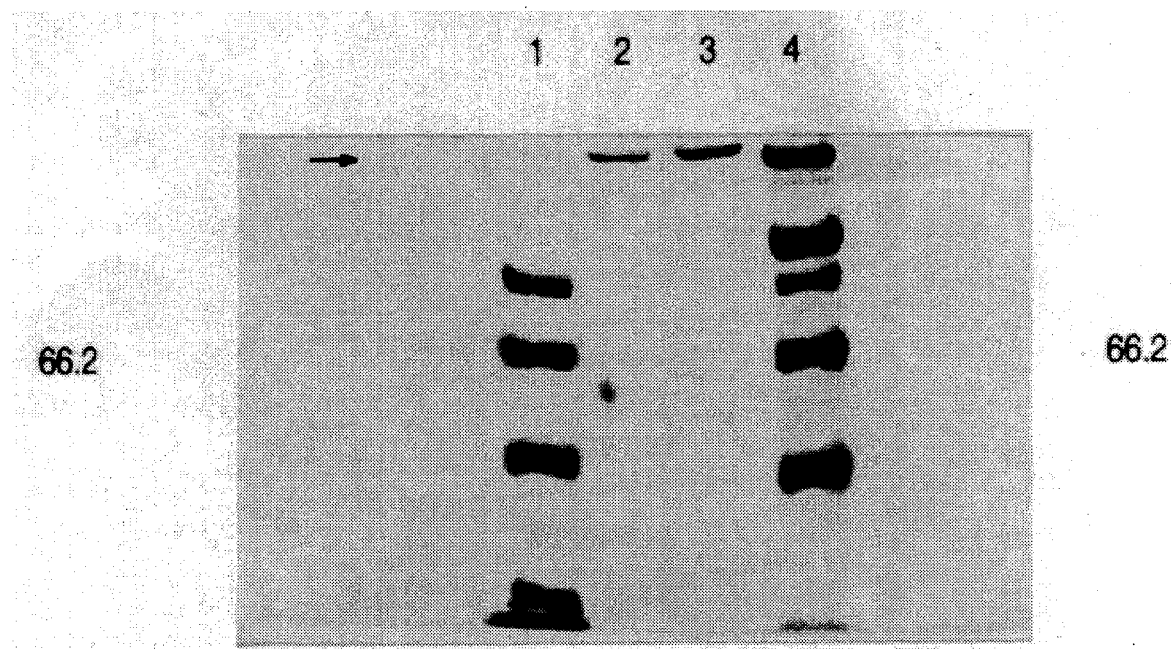
FIG. 1 shows SDS-PAGE analysis of purified *Clostridium difficile* toxin A.

The present invention relates to methods for treating cancer, and particularly colon and pancreatic cancer. In a preferred embodiment, the present invention contemplates using soluble *Clostridium difficile* toxin A to treat gastrointestinal tumors.

*Clostridium difficile* Toxins.

Toxigenic strains of *Clostridium difficile* produce at least two major potent toxins, an enterotoxin (toxin A) and a cytotoxin (toxin B). Lyerly, et al., Clin. Microbio. Rev. 1:1 (1988). Toxins A and B contribute to the syndrome of pseudomembranous colitis in patients and experimental animals undergoing antibiotic therapy, though toxin A is thought to be primarily responsible for these symptoms.

Characterization of this molecule has revealed that it has a mass of 308 kDa (deduced from the nucleotide sequence) and contains 38 contiguous repeating units located on the C-Terminal third of the molecule as deduced from the gene sequence. Dove et al., Infect. Immun. 58:480 (1990). It has been suggested that these repeating sequences may represent the cell receptor-binding region of the molecule as well as the binding site of the neutralizing PCG-4 monoclonal antibody. Fiorentini and Thelestam, Toxicon 29:543 (1991).

It is likely that distinct domains of this large and complex molecule may possess different functions. In this regard, the present invention contemplates toxin fragments, including peptides representing a portion of the molecule, in the treatment methods employed. In a preferred embodiment, the present invention contemplates the use of the 11-amino acid synthetic peptide with a terminal cysteine residue: CQTIDGKKYYFN-NH$_2$.

It is not intended that the invention be limited to toxin A fragments that are cytotoxic. In one embodiment, a synthetic peptide capable of binding to gastrointestinal tumor cells is conjugated to a cytotoxic protein (e.g., ricin) or other cytotoxic compound (e.g. anticancer drugs).

Toxin A is commercially available from Techlab Inc (Blacksburg, Va.). Toxin fragments may be made synthetically, biochemically (e.g. enzymatic cleavage of the native protein), and/or recombinantly.

In Vitro Methods.

The effect of toxin A on a variety of cultured cells has been observed by light and electron microscopy. Kushnaryov and Sedmak, Infect. Immun. 57:3914 (1989). Kushnaryov et al., Cytobios 64:181 (1990). Fiorentini et al., Infect. Immun. 58:2329 (1990). In CHO cells, it was discovered that toxin A is internalized by receptor-mediated endocytosis subsequently affecting the cytoskeleton and nucleus. Nuclear filaments comprised of actin, lamin, and vinculin transiently appeared between 2.5 and 4 hr of exposure to the toxin, coinciding temporally with the irreversibility of the cytopathic effect.

The present invention describes, in a study of 24 human cell lines and strains, that cells derived from human gastrointestinal tract malignancies (colon and pancreas) are extraordinarily sensitive to low doses of toxin A compared to cell derived from other sites (prostate, lung, breast, fibroblasts, and lymphoid malignancies). Kushnaryov et al., Cancer Res. 52:5096 (1992).

The present invention contemplates a screening assay utilizing the binding activity of toxin A. In one embodiment, a portion of a patient's tumor is obtained (e.g., by biopsy) and placed in tissue culture. Thereafter, the sensitivity of the tumor to toxin A is assessed by adding the toxin to the tissue culture and measuring for growth inhibition.

In Vivo Methods.

The present invention contemplates both diagnostic and therapeutic uses for toxin A in vivo. In one embodiment, binding of labelled toxin (e.g., radiolabelled, enzyme labelled, etc.) to patient tumor cells is measured in situ. In this embodiment, a diagnostic dose of the labelled toxin (or toxin fragment) is administered and the localization of the toxin on tumor cells is observed (i.e., in the manner of tumor imaging), indicating both the location of tumor cells (e.g., metastases) as well as the potential sensitivity of the tumor cells to a therapeutic dose of the toxin.

The present invention contemplates a therapeutic dose of the toxin administered to the patient (e.g., intravenously, intraperotoneally, etc.) followed by retardation of tumor growth. While the benefit conveyed by treatment according to the present invention is not dependent on the understanding of the mechanism(s) by which toxins achieve a therapeutic result, it is believed that the anticancer effects are accomplished by binding of the exogenously supplied toxin to tumor cell receptors.

Therapeutic Preparations and Combinations.

The present invention contemplates using therapeutic compositions of toxins to treat cancer. Where combinations are contemplated, it is not intended that the present invention be limited by the particular nature of the combination. The present invention contemplates combinations as simple mixtures as well as chemical hybrids. An example of the latter is where the toxin is covalently linked to a pharmaceutical. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for gastrointestinal cancer usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared.

The toxins of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); gm (grams); mg (milligrams); µg (micrograms); L (liters); ml (milliliters); µl (microliters); cm (centimeters); mm (millimeters); µm (micrometers); nm (nanometers); °C. (degrees Centigrade).

EXAMPLE 1

In this example, the purity of soluble toxin A is examined. Toxin preparations were obtained by growing *Clostridium*

*difficile* VPI strain 10463 in twelve 2-liter brain heart infusion dialysis flasks at 37° C. for three days. The initial step of the purification scheme involved ultrafiltration through an XM-100 membrane filter (Amicon Corp., Lexington, Mass.) with a thin-channel type concentrator. The retentate was washed with 1,500 ml of 50 mM Tris-HCl buffer (pH 7.5) at 4° C. and concentrated to a final volume of 40 to 50 ml.

The concentrated supernatant was loaded onto a DEAE-Sepharose CL-6B column (2.5 by 10 cm) which has been equilibrated with 50 mM Tris-HCl (pH 7.5). After the sample was loaded, the column was washed with 200 ml of 50 mM Tris-HCl (pH 7.5) containing 0.05M NaCl. The sample was eluted first with a 300-ml linear NaCl gradient in 50 mM Tris-HCl buffer (0.05 to 0.25 NaCl), followed by 150 ml of 50 mM Tris-HCl buffer containing 0.3M NaCl A second 300-ml linear gradient (0.3 to 0.6M NaCl) in the same buffer followed the 0.3 NaCl wash. Fractions were tested for cytotoxicity. The fractions with the highest activity were dialyzed against 1 liter of 0.01M sodium acetate buffer (pH 5.5). The dialysate was centrifuged to recover the precipitated.

A gradient (4–15%) polyacrylamide gel was used to estimate the molecular weight of toxin A. FIG. 1 shows SDS-PAGE analysis of purified *Clostridium difficile* toxin A. Lanes 1 and 4 are molecular weight markers. Lanes 2 and 3 show the mobility of the purified toxin (see arrow) when 0.4 and 0.8 micrograms, respectively, were added to the wells.

From FIG. 1 it is evident that the toxin is homogeneous. The preparation was thereafter stored as a filter-sterilized solution at 4° C. The level of endotoxin as measured by the Limulus lysate assay (Sigma, St. Louis, Mo.) was below the detection limit (0.5 endotoxin units/ml) for a 500-ng/ml solution of toxin A in minimal essential medium containing 2% fetal bovine serum.

EXAMPLE 2

In this example, the use of soluble toxin A is examined on cultured cell lines (see Table 1). Briefly, cells were distributed in 96-well plates at $5\times10^4$ cells/well and incubated at 36° C. overnight. The medium was exchanged for identical medium with 2% serum that contained serial 2-fold dilutions of toxin A starting at 500 ng/ml. Cells were incubated at 36° C. and toxicity was assessed by phase-contrast microscopy; cultures were observed every 1–2 h for 8 h and at 24 h. The cytotoxic dose, CTD-24, was defined as the lowest concentration that would lead to a cytopathic effect, i.e., cell rounding, of 100% of cells at 24 h.

TABLE 1

Designation And Origin Of Human Cell Lines And Strains[1]

| ORIGIN | CELL LINES OR STRAINS |
|---|---|
| Colonic carcinoma | SW1116, HCT116, SKCO-1, HT-29, KM12C, KM12SM, KM12L4, SW480 |
| Pancreatic carcinoma | BxPC-3, AsPC-1, Capan-2, MIA PaCa-2, Hs766T |
| Colon adenoma | VaCo 235 |
| Lung carcinoma | A549 |
| Prostate carcinoma | PC-3, DU-145 |
| Breast carcinoma | 009P, 013T |
| Lymphoma | Daudi, Raji |
| Breast epithelium | 006FA |
| Diploid fibroblast | HCS (human corneal stroma), MRC-5 |

TABLE 1-continued

Designation And Origin Of Human Cell Lines And Strains[1]

| ORIGIN | CELL LINES OR STRAINS |
|---|---|

[1]The SW1116, HT-29, SW480, Raji lymphoblastoid cells, and the pancreatic lines were obtained from the American Type Culture Collection. The KM12C, KM12L4, and KM12SM cells were obtained from Dr. J. Fidler, University of Texas, Houston, TX. The HCT116 and SKCO-1 cells were obtained from Dr. J. Schiller, University of Wisconsin, Madison, WI. VaCo 235 cells were obtained from J. Wilson, University Hospitals of Cleveland, Cleveland, OH. The PC-3 and DU-145 cells were obtained from Dr. G. Wilding, University of Wisconsin, Madison, WI. The 009P, 013T, and 006FA cells were provided by Dr. M. Hancock, Triton Biosciences, Alameda, CA. HCS fibroblasts were provided by Drs. W. O'Brien and J. Taylor, Medical College of Wisconsin, Milwaukee, WI. The MRC-5 diploid fibroblasts were provided by Dr. D. Carrigan, Medical College of Wisconsin, Milwaukee, WI.

Incubation of cells with toxin A leads to a cytopathic effect manifested by cell rounding and eventual cell death. CHO cells, a cell line sensitive to the cytopathic effect of the toxin, manifest rounding of all cells at concentrations of 100–150 ng/ml by 24 h. The selectivity of the cytopathic effect was studied on 24 human cell strains and lines derived from breast epithelial cells, diploid fibroblasts, carcinomas of the prostate, lung, breast, colon, pancreas, and malignant lymphoid tissue.

Figure 2:
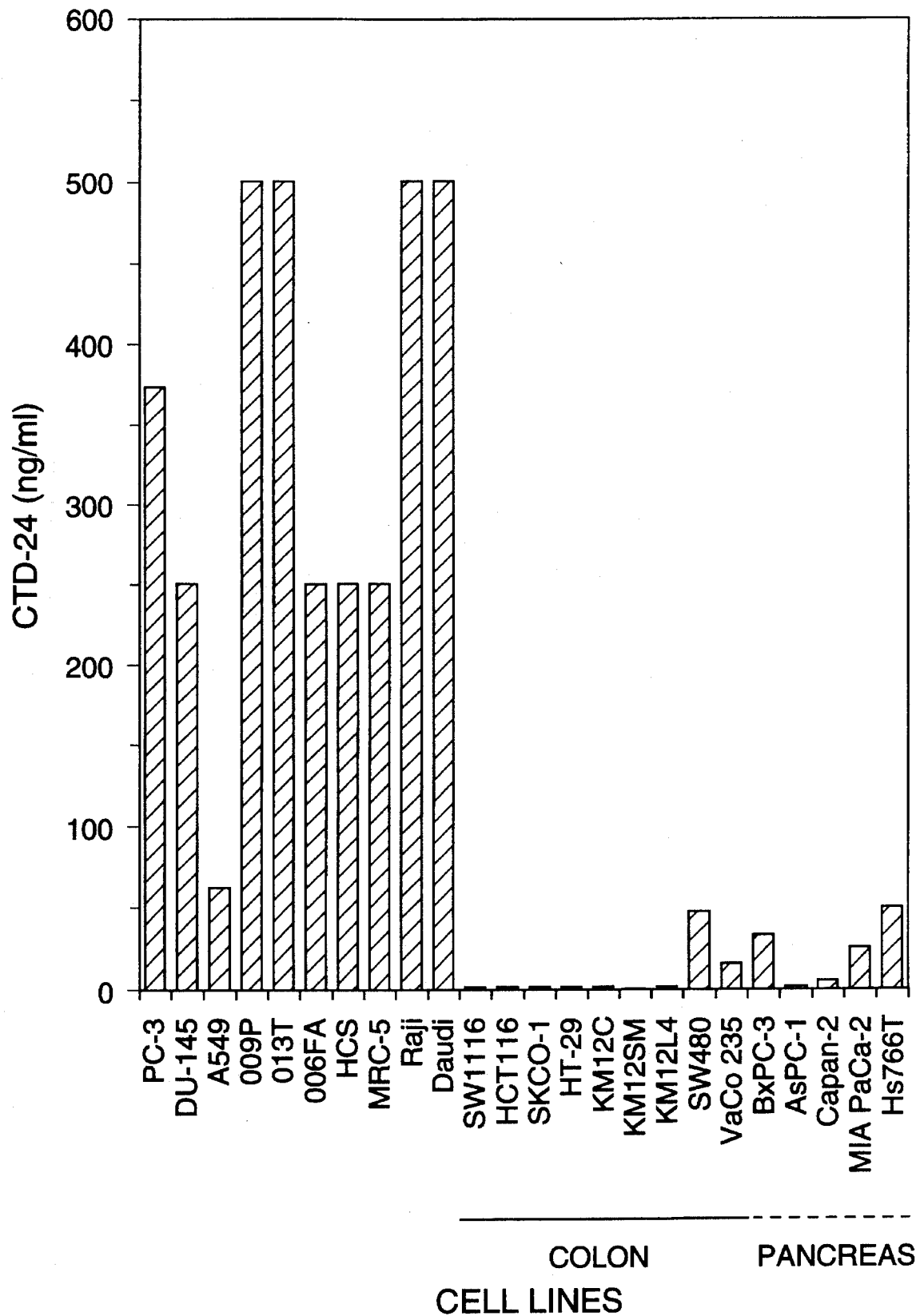
FIG. 2 is a bar graph showing differential sensitivity of tumor cell lines to toxin A in vitro.

Incubation of SKCO-1 colon carcinoma cells in the presence of toxin A caused an increase in refractility and retraction of the cytoplasm toward the nucleus, resulting in complete rounding of the cells and eventual cell death. The concentrations of toxin A that led to a cytotoxic effect on 100% of cells measured at 24 h (CTD-24) on different cell lines and strains are presented in FIG. 2. All eight lines of colonic carcinoma and five lines of pancreatic carcinoma were extraordinarily sensitive to the toxin. Seven colon and two pancreas cell lines were affected at concentrations as low as 1–5 ng/ml ($10^{-12}$ to $10^{-11}$M), whereas cells from non-gastrointestinal tract sites required 60 to greater than 500 ng/ml to achieve an equivalent cytotoxic effect.

Colon carcinoma cell lines having different metastatic behavior in a nude mouse model were equally sensitive to the toxin in vitro. The highly metastatic KM12L4 and KM12SM cell lines were affected at the same concentration (1–2 ng/ml) as the poorly metastatic parental line KM12C originally derived from a Dukes' $B_2$ tumor. In addition, a colon cell line derived from a villous adenoma of the rectum, VaCo 235, was affected at a mean concentration of 16 ng/ml. Thus, the high sensitivity to the cytopathic effect of toxin A was a uniform characteristic of the colon cell lines evaluated regardless of their degree of malignant differentiation or metastatic potential.

By contrast Daudi and Raji cell lines, both of lymphoblastoid origin, were unaffected by toxin A at the highest tested concentration of 500 ng/ml during 5 days of culture as determined by counting of viable cells. This clearly indicates the level of specificity of the interaction of the toxin at the cellular level.

To confirm the results of the visual method of cytotoxicity testing, the MTT colorimetric assay was employed for measuring cell respiratory activity to assess cell killing on selected sensitive (SKCO-1, HCT116, AsPC-1, and Capan-2) and resistant (DU-145 and PC-3) cell lines at different toxin concentrations. At 12.5 ng/ml, the absorbance of the sensitive cell lines incubated with toxin for 3 days ranged from 15 to 30% of untreated controls compared to 93 to 100% for the resistant cell lines. Furthermore, the decrease in absorbance, i.e., diminished cell respiratory activity, correlated with cell rounding. Similar results were observed at higher toxin concentrations.

To evaluate the morphological changes over time associated with cell rounding, selected sensitive cell lines were evaluated by electron microscopy. Rounded cells demonstrated vacuolization, autolysis, and complete disintegration by 48–72 h following toxin exposure, confirming that rounding resulted in cell death (not shown).

EXAMPLE 3

In this example, the kinetics of the response to soluble toxin A is examined. The kinetics of the cytotoxic effect was evaluated by counting a minimum of 200 cells at frequent intervals as noted, and the percentage of rounded cells calculated. CHO cells, previously characterized with respect to its sensitivity to toxin A, were used as a reference control cell line. The data were evaluated statistically in the two-tailed Student's t test.

Figure 3:
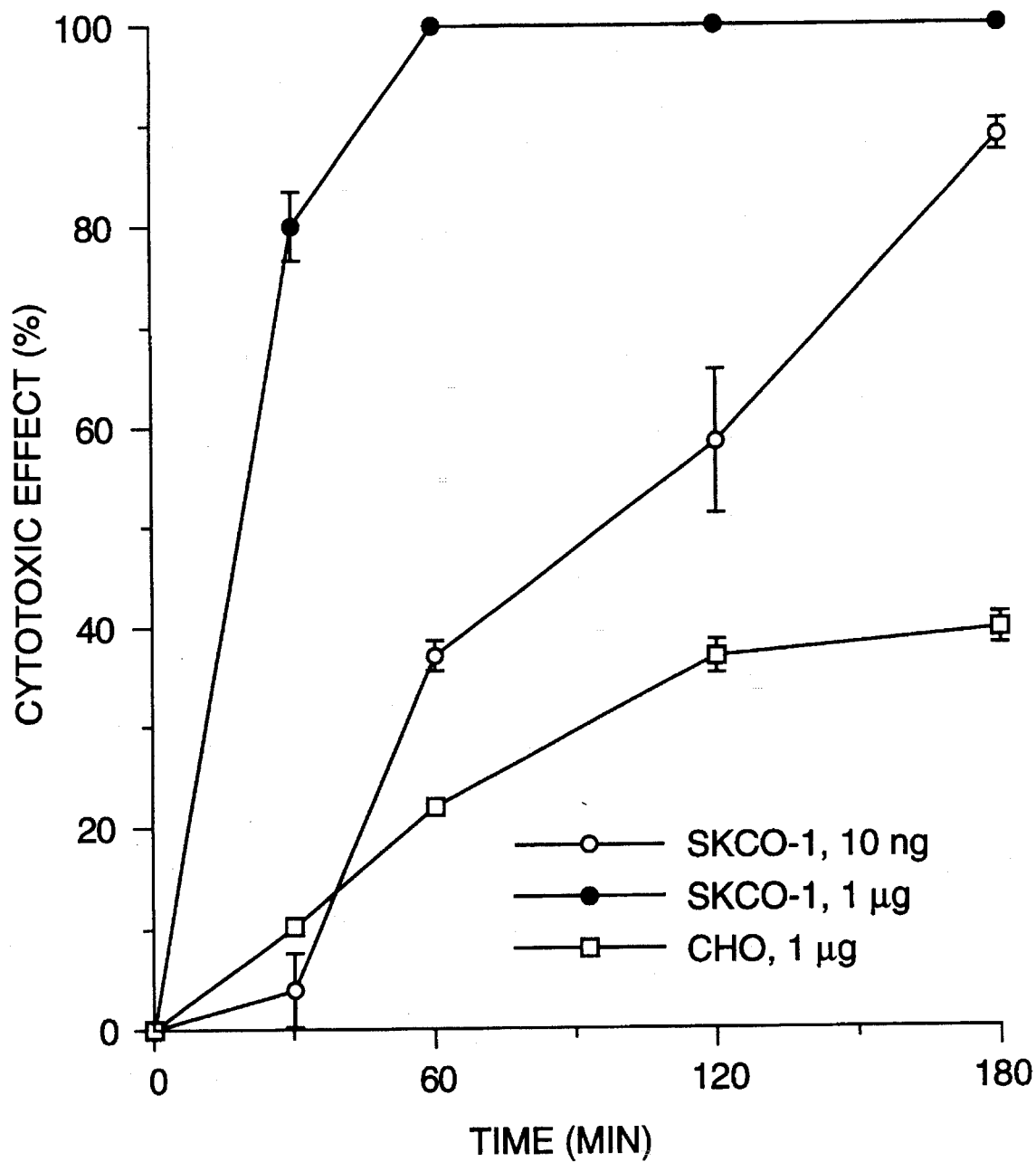
FIG. 3 graphically shows the kinetics of toxin A cytotoxicity on cultured tumor cells.

The kinetics of the cytopathic effect of toxin A for SKCO-1 and CHO cells is shown in FIG. 3. An effect on SKCO-1 cells was noted within 30 min of exposure to 1 µg/ml of the toxin, equivalent to 500×CTD-24. At a concentration of 10 ng/ml (5×CTD-24), rounding of cells was less rapid; nevertheless, most cells were rounded by 3 h of exposure. The kinetics of cell rounding for CHO cells at 1 µg/ml (9×CTD-24) was comparable to that observed for SKCO-1 cells exposed to the lower toxin concentration. In separate experiments, HCT116 cells were rapidly affected at toxin concentrations of 10 ng/ml and 1 µg/ml in a manner identical to that observed for SKCO-1 cells (results not shown).

EXAMPLE 4

In this example, the use of soluble toxin A in vivo is examined. The efficacy and toxicity of toxin A was demonstrated in a nude mouse model of subcutaneously inoculated HCT 116 colon carcinoma cells. HCT 116 cells were injected subcutaneously in the right flank/thorax region of 5 week old male nude mice (Taconic Farms) at a dose of $2 \times 10^6$ cells/mouse. Tumors were measured weekly in three dimensions. Toxin A, freshly diluted in Hank's balanced salt solution (HBSS), was administered intraperitoneally at a dose of 5–10 ng/mouse in 0.5 ml. Control groups consisted of non-tumor bearing mice receiving toxin only and tumor-bearing mice receiving injections of HBBS only. At 8 weeks, one animal each from the treatment and tumor-bearing control groups underwent MRI scanning and was sacrificed for histologic evaluation of tumors.

Figure 4:
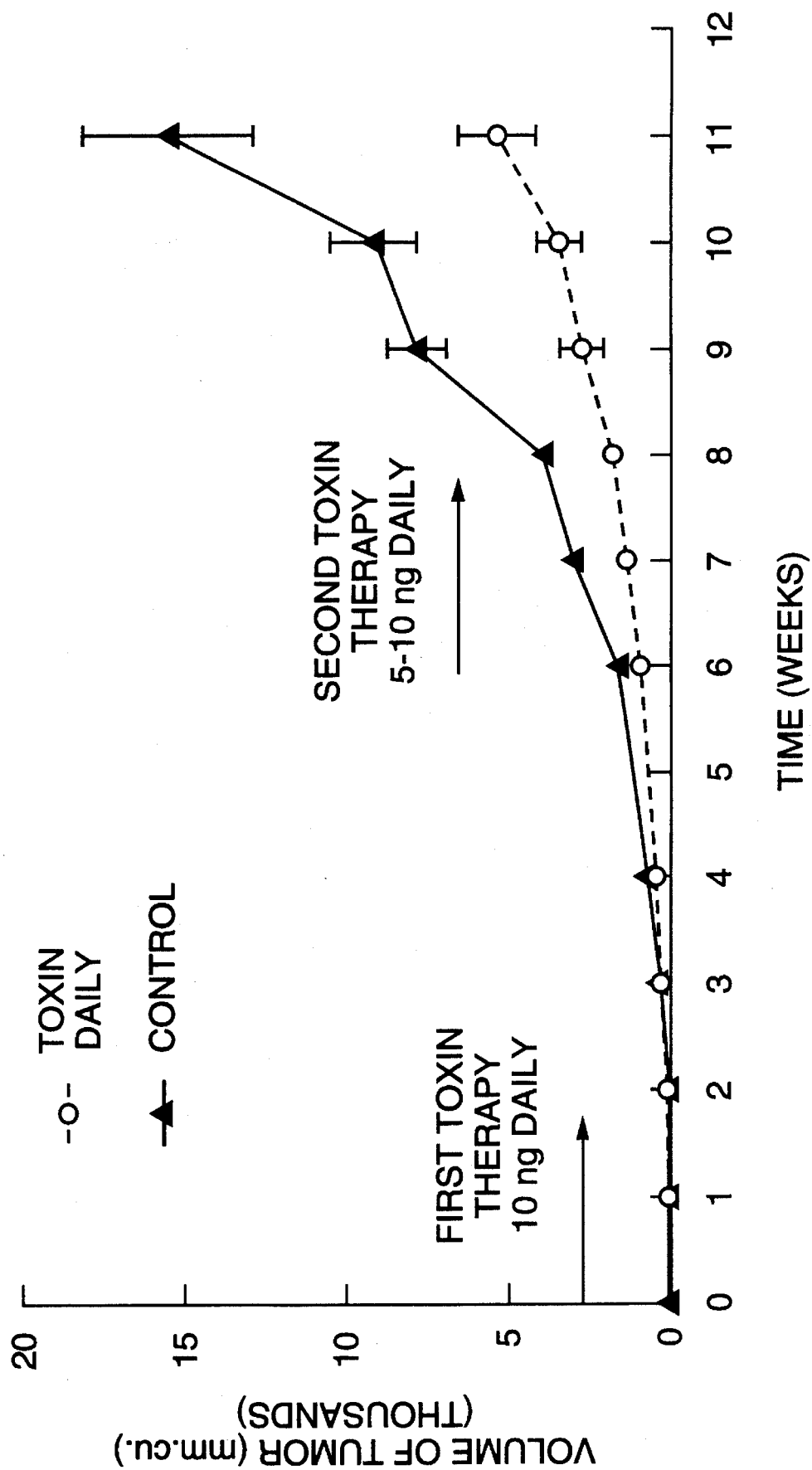
FIG. 4 graphically shows the growth of human colon cancer in vivo with and without treatment according to the method of the present invention.

A statistically significant retardation of tumor growth was observed in the treated group compared to the control resulting in at least a 65% reduction in tumor volume by week 9 (see FIG. 4). There was no toxin-related mortality in the tumor-bearing animals, though 2/10 died in a non-tumor control group receiving toxin. Redlich et al., Proc. Am. Assoc. Cancer Res. (1992). The treated animals showed no outward indication of systemic toxicity.

Figure 5:
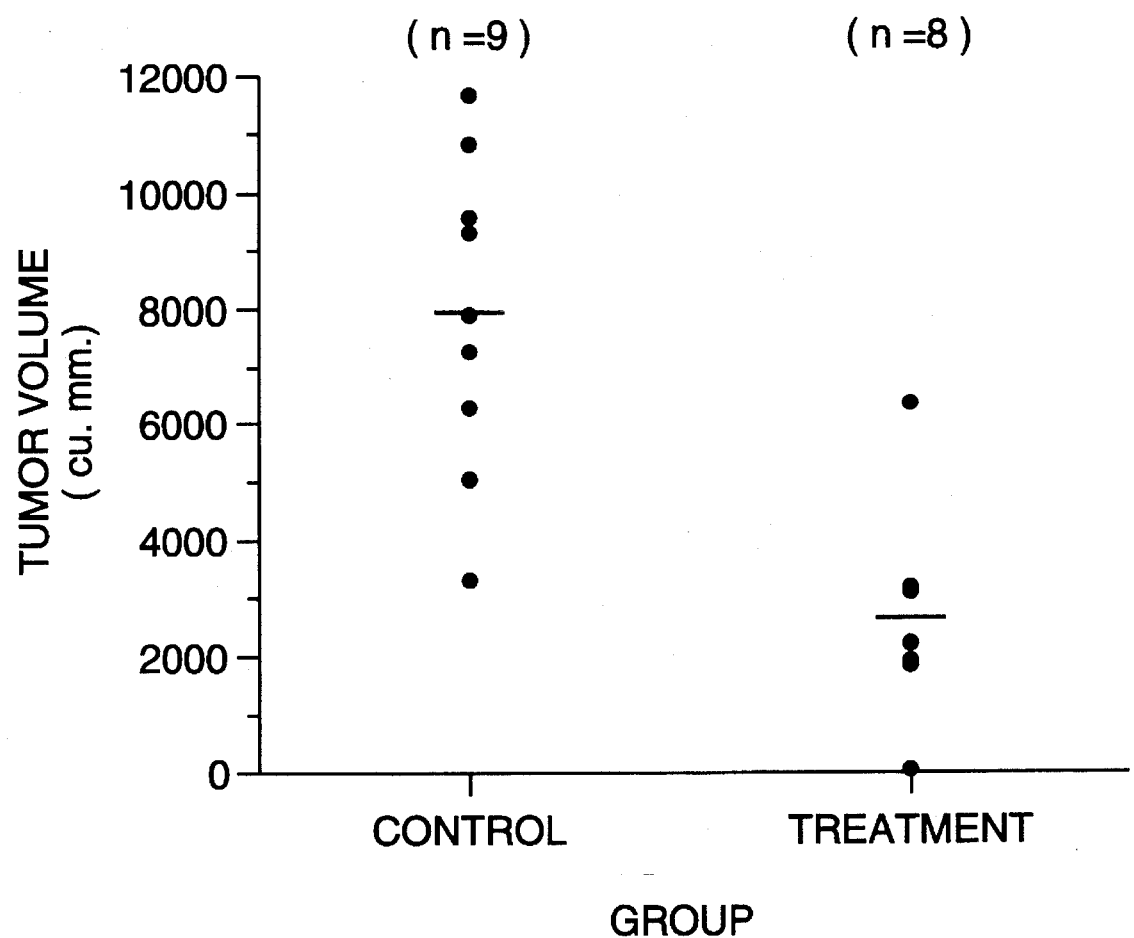
FIG. 5 is a scattergram showing the individual variation of tumor growth when subjected to the treatment method of the present invention.

FIG. 5 is a scattergram showing the individual variation of tumor growth when subjected to the treatment method of the present invention. Tumors from week 9 of growth from control (n=9) and toxin-treated (n=8) groups are represented. The difference between the means (horizontal bar) of the two groups is statistically significant (P<0.002). The decreased scatter of the tumor volumes in the treated group is apparent; one mouse in the group had complete regression of palpable tumor following two courses of toxin therapy.

Histological analysis of the tumors (8 weeks of growth) in the toxin treated animal demonstrated a great deal of central necrosis with ulceration of the epidermis and invasion of the epidermis (not shown). Analysis of the control (untreated) animal with respect to its tumor demonstrates central necrosis as well, but there was no invasion of the epidermis by the tumor cells. In addition, there appears to be more viable tumor present and less necrosis in the control animal's tumor compared to the tumor in the treated animal.

EXAMPLE 5

In this example, the effect of toxin A on normal cells is described. Analysis was performed of organs from mice given lethal doses (40 ng) of toxin and harvested the following day, specifically, mice numbered 40-1 and 40-2. Inspection of sections of liver revealed vascular congestion with the presence of blood lakes. This pattern of hemorrhage is similar to that of peliosis hepatis. There is also some hepatocellular necrosis.

Analysis of the terminal ileum, colon and kidney demonstrated no pathologic change. This indicates that the toxicity at lethal doses involves the liver and does not involve damage to normal gastrointestinal cells.

EXAMPLE 6

In this example, the preparation of a toxin A fragment conjugate is described. The synthetic peptide CQTIDGKKYYFN-NH$_2$ (SEQ ID No: 1) was prepared commercially (Multiple Peptide Systems, San Diego, Calif.) and validated to be >80% pure by high-pressure liquid chromatography. The eleven amino acids following the cysteine residue represent a consensus sequence of a repeated amino acid sequence found in toxin A that is involved in cell surface binding. Wren et al., Infection and Immunity 59:3151 (1991). The cysteine was added to facilitate conjugation to other proteins.

In order to prepare a protein for conjugation, it is dissolved in buffer (e.g., 0.01M NAPO$_4$, pH 7.0) to a final concentration of approximately 20 mg/ml. At the same time n-maleimidobenzoyl-N-hydroxysuccinimide ester ("MBS" available from Pierce) is dissolved in N,N-dimethyl formamide to a concentration of 5 mg/ml. The MBS solution, 0.51 ml, is added to 3.25 ml of the protein solution and incubated for 30 minutes at room temperature with stirring every 5 minutes. The MBS-activated protein is then purified by chromatography on a Bio-Gel P-10 column (Bio-Rad; 40 ml bed volume) equilibrated with 50 mM NaPO$_4$, pH 7.0 buffer. Peak fractions are pooled (6.0 ml).

Lyophilized toxin A peptide (20 mg) is added to the activated protein mixture, stirred until the peptide is dissolved and incubated 3 hours at room temperature. Within 20 minutes, the reaction mixture becomes cloudy and precipitates form. After 3 hours, the reaction mixture is centrifuged at 10,000×g for 10 min and the supernatant analyzed for protein content. The conjugate precipitate is washed three times with PBS and stored at 4° C.

From the above it should be clear that the present invention provides an approach to gastrointestinal cancer that is reliably tumoricidal. Importantly, the treatment is effective with minimal toxicity to normal gastrointestinal cells.

We claim:

1. A method of treating gastrointestinal cancer, comprising contacting tumor tissue with a preparation comprising *Clostridium difficile* toxin A.

2. The method of claim 1, wherein the cancer is colon cancer.

3. The method of claim 1, wherein the cancer is pancreatic cancer.

4. The method of claim 1, wherein said toxin is administered intravenously to a cancer patient.

5. A method of treating cancer, comprising:

a) providing i) a patient with gastrointestinal cancer, and ii) a preparation comprising *Clostridium difficile* toxin A in an aqueous solution in therapeutic amounts that is intravenously injectable; and b) intravenously injecting said toxin into said patient.

6. The method of claim 5, wherein said cancer is colon cancer.

7. The method of claim 5, wherein said cancer is pancreatic cancer.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 12 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:1:

Cys Gln Thr Ile Asp Gly Lys Lys Tyr Tyr Phe Asn
1               5                       10